United States Patent
Rambod et al.

(10) Patent No.: US 8,109,876 B1
(45) Date of Patent: Feb. 7, 2012

(54) NONINVASIVE TECHNIQUE FOR IDENTIFICATION OF STRUCTURAL INTEGRITY OF BJORK SHILEY CONVEXO-CONCAVE MECHANICAL HEART VALVES

(75) Inventors: Edmond Rambod, Los Angeles, CA (US); Morad Isaacian, Beverly Hills, CA (US)

(73) Assignee: Bioquantetics, Inc., Los Angeles, CA (US)

( * ) Notice: Subject to any disclaimer, the term of this patent is extended or adjusted under 35 U.S.C. 154(b) by 1201 days.

(21) Appl. No.: 11/807,789

(22) Filed: May 29, 2007

Related U.S. Application Data

(60) Provisional application No. 60/830,450, filed on Jul. 13, 2006.

(51) Int. Cl.
*A61B 8/00* (2006.01)
(52) U.S. Cl. ........................... 600/437; 600/438
(58) Field of Classification Search ............ None
See application file for complete search history.

(56) References Cited

U.S. PATENT DOCUMENTS

| | | | |
|---|---|---|---|
| 5,903,516 A | 5/1999 | Greenleaf | |
| 5,921,928 A | 7/1999 | Greenleaf | |
| 2007/0016031 A1* | 1/2007 | Mourad et al. | 600/437 |

OTHER PUBLICATIONS

S. C. Chan, R. Clifford, S. Majumdar, N. Nair, S. Ramakrishnan, Y. Li, P. Ramuhalli, L. Udpa and S. S. Udpa, "Novel methods for detecting fractures in prosthetic heart valves," Insight: Nondestructive Testing and Condition Monitoring, vol. 47, No. 1, pp. 15-19, Jan. 2005.*
Chia R. Finite element analysis of vibrations of the Bjork-Shiley convexo-concave heart valve. Proc Annu IEEE Symp Computer-Based Med Sys. 1994;7:48-52.*
van Neer, P. L. M. J. et al. "Detecting broken struts of a Bjork-Shiley heart valve using ultrasound: a feasibility study", Ultrasound in Medicine and Biology, vol. 32, No. 4, pp. 503-512 (2006).*
Blot WJ et al., "Risks of fracture of Bjork-Shiley 60 degree convexo-concave heart valve . . . " J. Heart Dis. 10, 202-209 (2001).
De Mol Ba et al., "Non-destructive assessment of 62 Dutch Bjork-Shiley convexo-concave heart valves", Eur. J. Cardiothorac. Surg. VI, 708-708. discussion 708-709 (1997).
Candy JV et al., "Processing of prosthetic heart valve sounds for single leg separation . . . ", J. Acoust-Soc. Am. 97,,3663-3673 (1995).
Plemons TD et al., "Acoustic classification of the state of artifical heart valves," J. Acoust. Soc. Am 2326-2333 (1995).

(Continued)

*Primary Examiner* — Long V. Le
*Assistant Examiner* — Bradley Impink
(74) *Attorney, Agent, or Firm* — Thomas I. Rozsa

(57) ABSTRACT

The present invention is a non-invasive method and apparatus to determine the structural integrity of an implanted BSCC by insonifying the implanted heart valve with a megahertz frequency to cause the structural components of the heart valve to vibrate at a kilohertz frequency range to cause the individual structural components of the heart valve being investigated to vibrate at their resonant frequency. From experimental testing, the Applicants have established resonant frequency ranges of certain structural components of the BSCC which indicate that at certain resonant frequency ranges the heart valve components are intact. At other resonant frequency ranges, certain components are in danger of breaking. At other frequency ranges, the components of the heart valve are fractured. Through the present invention, the condition of the BSCC can be determined in order to provide a clinical determination as to whether or not the implanted BSCC needs to be replaced.

14 Claims, 4 Drawing Sheets

OTHER PUBLICATIONS

Eberhardt AC, et al., "Acoustic characterization of mechanical valve condition and loading", J. Heart Valve Dis. 4, 649-658, disc. 658-659 (1995).

Bjork VO, "A new tilting disc valve prostheis", Scand J Thorac Cardiovasc. Surg. 3, 1-10 (1969).

Bjork VO, "The improved Bjork-Shiley fitting disc valve prosthesis." Scand. J. Thorac. Cardiovasc. Surg. 12. 81-84 (1978).

Bjork VO, "The optimal opening angle of the Bjork-Shiley tilting disc valve prosthesist", Scand. J. Thorac. Cardivasc. Surg. 15, 223-227 (1981).

Wieting DW et al., "Strut fracture mechanisms of the Bjork-Shiley convexo-concave heart valve", J. Heart Valve Dis. 8, 206-217 (1999).

Wenzel TC, et al., "Welding metallurgy's putative influence on Bjork-Shiley convexo-concave valve outlet strut failures." J. Heart Valve Dis. 8,218-231 (1999).

Walker AM et al., "Manufacturing characteristics associated with strut fracture in Bjork-Shiley 60 degrees convexo-concave heart valves," J. Heart Valve Dis. 4, 640-648 (1995).

Kallewaard M, et al. "Which manufacturing characteristics are predictors of outlet strut fracture . . . " THe Bjork Study Group. J. Thorac. Cardiovasc. Surg. 117. 766-775 (1999).

Flannery, B et al., "Three-dimensional x-ray microtomography", Science 237, 1439-1444 (1987).

G.R. Tor, "The Acoustic Radiation Force", Am. J. Phys. 52, 402-408 (1984).

R.T. Beyer "Radiation Pressure in a Sound Wave", Am. J. Phys. 18, 25-29 (1950).

P.M.T. Wells, "Biomedical Ultrasonics", Academic Press, New York, 1977.

O'Neill WW et al., "Radiographic detection of single strut leg separations . . . " N. Engl. J. Med. 333. 414-419 (1995).

Chandler JG et al., "Radiographic detection of single strut leg separations . . . ". World J. Surg. 20, 953-959, disc. 959-960 (1996).

Hopper KD et al., "In vivo accuracy of two radiographic systems . . . ". J. Thorac. Cardiovasc. Surg. 115, 582-590 (1998).

De Mol Ba et al., "The complexity of external acoustic detection of defects in Bjork-Shiley convexo-concave heart valves." Artif. Organs 25, 63-67 (2001).

Fatemi M et al., "Vibro-acoustography: An imaging modality based on ultrasound-stimulated acoustic emission," Proc. Natl. Acad. Sci. USA 96, 6603-6608 (1999).

M. Fatemi et al., "Vibro-Acoustography: An Imaging Modality Based on Ultrasound-Stimulated AcoustIc Emission,", Proc. Natl. Acad. Sci. 96, 6603-6608 (1999).

Chia, R. "Finite Element Analysis of Vibrations of the Bjork Shiley Convexo-Concave Heart Valve", Seventh Annual IEEE Symposium on Computer-Based Medical Systems, 1994, 48-52.

Avrom Brendzel et al., "Three-dimensional Imaging of Fractures in Outlet Struts of Bjork Shiley Convexo-Concave Heart Valves . . . ", J. Heart Valve Dis, vol. 11, No. 1, Jan. 2002, 114-120.

* cited by examiner

Insonification and Excitation using two Single Element Transducer

Insonification and Excitation using one Dual-Element Transducer

Insonification and Excitation using one Single-Element Transducer and Amplitude Modulation

NONINVASIVE TECHNIQUE FOR IDENTIFICATION OF STRUCTURAL INTEGRITY OF BJORK SHILEY CONVEXO-CONCAVE MECHANICAL HEART VALVES

The present invention claims the benefit under Title 35, United States Code §119(e) of Provisional Application No. 60/830,450 filed on Jul. 13, 2006.

BACKGROUND OF THE INVENTION

1. Field of the Invention

The field of the present invention relates to medical testing to determine the condition of an implanted heart valve in order to determine whether the implanted heart valve is intact and is not in imminent danger of malfunctioning due to structural defects or whether the implanted heart valve is in various stages of possible failure which necessitates the replacement of the valve through surgery.

2. Description of the Prior Art and Discovered Defects in the Bjork Shiley Convexo-Concave Mechanical Heart Valves 2.1 General Prior Art Background The following prior art references are listed in superscript in the text below:
1. Bjork V O, "A new tilting disc valve prosthesis," Scand J Thorac Cardiovasc. Surg. 3, 1-10 (1969).
2. Bjork V O, "The improved Bjork-Shiley fitting disc valve prosthesis." Scand. J. Thorac. Cardiovasc. Surg. 12. 81-84 (1978).
3. Bjork V O, "The optimal opening angle of the Bjork-Shiley tilting disc valve prosthesis," Scand. J. Thorac. Cardiovasc. Surg. 15, 223-227 (1981).
4. Wieting D W, Eberhardt A C, Reul H, Breznock E M, Schreck S G. Chandler J G. "Strut fracture mechanisms of the Bjork-Shiley convexo-concave heart valve," J. Heart Valve Dis. 8, 206-217 (1999).
5. Wenzel T C, Mannig C R, Chandler J G, Williams D F, "Welding metallurgy's putative influence on Bjork-Shiley convexo-concave valve outlet strut failures." J. Heart Valve Dis. 8, 218-231 (1999).
6. Walker A M, Punch D P, Sulsky S I, Dreyer N A. "Manufacturing characteristics associated with strut fracture in Bjork-Shiley 60 degrees convexo-concave heart valves," J. Heart Valve Dis. 4, 640-648 (1995).
7. Kallewaard M, Algra A, Defauw J. van der Graaf Y, "Which manufacturing characteristics are predictors of outlet strut fracture in large sixty-degree Bjork-Shiley convexo-concave mitral valves?" The Bjork Study Group. J. Thorac. Cardiovasc. Surg. 117. 766-775 (1999).
8. Blot W J, Omar R Z, Kallewaard M, et al. "Risks of fracture of Bjork-Shiley 60 degree convexo-concave prosthetic heart valves: Long-term cohort follow up in the UK, Netherlands and USA," J. Heart Valve Dis. 10, 202-209 (2001).
9. de Mol B A, Overkamp P J, van Gaalen G L, Becker A E, "Non-destructive assessment of 62 Dutch Bjork-Shiley convexo-concave heart valves," Eur. J. Cardiothorac. Surg. VI, 703-708. discussion 708-709 (1997).
10. Candy J V, Jones H E, "Processing of prosthetic heart valve sounds for single leg separation classification," J. Acoust-Soc. Am. 97, 3663-3673 (1995).
11. Plemons T D, Hovenga M, "Acoustic classification of the state of artificial heart valves," J. Acoust. Soc. Am. 97, 2326-2333 (1995).
12. Eberhardt A C, Chassaing C E, Ward M A, Lewandowski S J, "Acoustic characterization of mechanical valve condition and loading," J. Heart Valve Dis. 4, 649-658, discussion 658-659 (1995).
13. Dow J J, Plemons T D, Scarbrough K, et al. "Acoustic assessment of the physical integrity of Bjork-Shiley convexo-concave heart valves," Circulation, 95, 905-909 (1997).
14. O'Neill W W, Chandler J G, Gordon R E, et al. "Radiographic detection of single strut leg separations in Bjork-Shiley convexo-concave mitral valves." N. Engl. J. Med. 333, 414-419 (1995).
15. Chandler J G, Hirsch J L, O'Neill W W, et al. "Radiographic detection of single strut leg separations as a putative basis for prophylactic explanation of Bjork-Shiley convexo-concave heart valves," World J. Surg. 20, 953-959, discussion 959-960 (1996).
16. Hopper K D. Gilchrist 1C, Landis J R, et al. "In vivo accuracy of two radiographic systems in the detection of Bjork-Shiley convexo-concave heart valve outlet strut single teg separations." J. Thorac. Cardiovasc. Surg. 115, 582-590 (1998).
17. de Mol B A, Cromkeecke M E, Groen J G, Faber G, van der Heiden M S, Ongkiehong L, "The complexity of external acoustic detection of defects in Bjork-Shiley convexo-concave heart valves," Artif. Organs 25, 63-67 (2001).
18. Fatemi M, Greenleaf J F, "Vibro-acoustography: An imaging modality based on ultrasound-stimulated acoustic emission," Proc. Natl. Acad. Sci. USA 96, 6603-6608 (1999).
19. Flannery B, Deckman H, Roterge W, D'Amico K, "Three-dimensional x-ray microtomography," Science 237, 1439-1444 (1987).
20. F. Burny, "Monitoring of Orthopedic Implants: A Biomaterials-Microelectronics Challenge," Elsevier Science, 1993.
21. M. A. Barbosa, "Imaging Technics in Biomaterials: Digital Image Processing Applied to Orthopedic and Dental Implants," Elsevier Science, 1994.
22. P. M. Morse and U. Ingard, "Theoretical Acoustics," McGraw-Hill, New York 1968.
23. L. F. Kinsler et al., "Fundamentals of Acoustics" (4$^{th}$ ed.) John Wiley, NY 1999.
24. G. R. Tor, "The Acoustic Radiation Force" Am. J. Phys. 52, 402-408 (1984).
25. R. T. Beyer, "Radiation Pressure in a Sound Wave" Am. J. Phys. 18, 25-29 (1950).
26. (a) J. D. N Cheeke, "Fundamentals and Applications of Ultrasonic Waves," CRC Print 2002; (b) P. M. T. Wells, "Biomedical Ultrasonics," Academic Press, New York, 1977.
27. J. F. Greenleaf and M. Fatemi-Booshehri, "Acoustic Force Generation for Detection, Imaging and Information Transmission Using the Beat Signal of Multiple Intersecting Sonic Beams," (May 11, 1999) U.S. Pat. No. 5,903,516.
28. J. F. Greenleaf and M. Fatemi-Booshehri, "Acoustic Force Generation by Amplitude Modulation of Sonic Beams," (Jul. 13, 1999) U.S. Pat. No. 5,921,928.
29. M. Fatemi and J. F. Greenleaf, "Vibro-Acoustography: An Imaging Modality Based on Ultrasound-Stimulated Acoustic Emission," Proc. Natl. Acad. Sci. 96, 6603-6608 (1999).
30. Chia, R., "Finite Element Analysis of Vibrations of the Bjork Shiley Convexo-Concave Heart Valve," Seventh Annual IEEE Symposium on Computer-Based Medical Systems, 1994, 48-52

31. Avrom Brendzel, Edmond Rambod, Steven M. Jorgensen, Denise A. Reyes, Michael Chmelik, Erik Ritman, "Three-dimensional Imaging of Fractures in Outlet Struts of Bjork Shiley Convexo-Concave Heart Valves by Micro-computed Tomography in vitro", J. Heart Valve Dis, Vol 11. No. 1, January 2002, 114-120.

The Bjork-Shiley Convexo-Concave (BSCC) heart valve was initially approved for patient use in 1979. The BSCC valve was suggested to be an improvement on the earlier RS (radial spherical) model based on a more physiologic flow profile and reduced thrombogenicity.[1-3] Soon after its introduction isolated fractures of the outlet strut began to be reported and their continued occurrence led to the withdrawal of the valve in 1986. During that seven-year period over 86,000 valves were implanted. This followed a number of reports of valve dysfunction due to structural failure, leading to patient death. Failure risk assessments have been reported.[6-8] To date more than 600 fractures have been reported with roughly 60% being fatal.

Fatigue and modeling studies have indicated that outlet strut fracture occurs in two phases with initial fracture of one of the legs of the outlet strut (Single leg separation or SLS) followed after a variable period of time by fracture of the second leg with resultant separation of the outlet strut, escape of the occluding disk and valve failure. Different technologies have been used to device a diagnostic that will identify structural imperfections in the BSCC heart valve.[4]

The current technology focuses on the active acoustic method in which an external source generates sound waves at varying, controlled frequencies within the range of natural resonance of the outlet struts. Finite element modeling, experimental, and in vitro flow studies have shown that the outlet strut vibrates at different characteristic frequencies when it is intact (~7 KHz), or when it is cracked (2 KHz and ~4 KHz)[11]. Insonifying the strut at a close or similar frequency by an external source will induce resonance that can be detected by an external sensor and thereby define the physical state of the outlet strut. The active acoustic approach has the theoretic advantage that the outlet strut can be excited and the resulting vibrations (emitted frequencies) can be sampled during a specific period within a cardiac cycle when the valve is closed. The resulting signals are thus free of noisy valve opening and closure sounds. This controlled classification method is in contrast to passive acoustic methods (the detection of the random vibrations induced in the outlet strut by opening and closure of the disc) where vibrations are only present during a limited time window and require sophisticated signal extraction and noise-elimination procedures to separate the desired frequencies from the higher amplitude disc impact signals.

2.2 Description of the BSCC and Prior Art Test to Attempt to Locate Structural Defects in the Implanted BSCC In order to describe the invention in full, we will provide a detailed description of one kind of implanted heart valve substitutes namely, the Bjork-Shiley Convexo-Concave (BSCC) mechanical valve. Periodic evaluation of the health of this valve is very critical and present imaging diagnostics modalities have failed to reliably verify the status of the valve integrity, by discovering the possible existence of microscopic fractures of the outlet strut. The BSCC valve (FIG. 1) consists of the following components, a flange (orifice ring) 1 and an inlet strut 4 fabricated as a single piece from a bar of Haynes 25 alloy; an outlet strut 2 formed from Haynes 25 alloy wire; a pyrolytic carbon-coated graphite disc 3 that occludes blood flow in its closed position, and allows blood flow in its open position; and a fabric sewing cuff 5 that surrounds the flange and that is sutured to the patient's heart tissue at implant. The outlet strut wire was formed into a W-shape, with the free ends of the legs of the W being attached to the flange by tungsten-inert-gas welding without filler material.[5, 9] The outlet strut and inlet strut limit the motion of the disc and prevent its escape as it passively cycles between the open and closed positions. The disc opens to either 60° or 70°, depending on the specific BSCC model.[7] Embedded within the disc is a tantalum C-ring radio-opaque marker. The mitral and aortic implant versions of the BSCC valve differed only in the shape of the sewing cuff. The valve was supplied in several sizes, with sizes 31 and 33 mm using the same metal and disc components ('valve body') as the size 29 mm valve, but with larger sewing cuffs.

Valve dysfunction consists of embolization of the disc due to structural failure of the outlet strut (outlet strut fracture, OSF), which has been attributed to a two-step fatigue process induced by cardiac cycle loading. In the first step, a fatigue crack develops in one leg of the outlet strut, and after a currently unpredictable length of time (which varies from case to case), leads to a through-fracture in that leg—a condition called single-leg separation (SLS). After SLS develops, the continued structural integrity of the other leg prevents disc escape. Wear burnishing of the fracture faces in the SLS leg occurs during the period that the other leg maintains its integrity.[5] In the second step, which may not occur in each BSCC valve having an SLS strut ('SLS-BSCC valve'), a fatigue crack develops in the second leg and, after an additional unpredictable and variable length of time, that leg also experiences fatigue failure, leading to disc escape. Because only a small fraction of BSCC valves apparently will fail by OSF during the patient's natural lifetime, and since valve replacement surgery itself carries a significant risk, it is desirable to develop a rationale for prophylactic BSCC valve replacement. To identify patients with defective valves, several groups have investigated screening methods including passive acoustic monitoring of valve closing or opening[10-13] and radiographic imaging of fractured struts.[14-16] However, so far such methods have not been able to reliably detect SLS-BSCC valves with sufficient specificity in vivo.[16-17]

Variations in outlet strut fracture morphology, including partial-thickness fractures (cracks), fracture faces in contact, fracture faces separated, and laterally displaced fracture faces, and variations in the position of fracture relative to the welded section of the strut, have been reported for a group of SLS-BSCC valve explants that were examined by optical and scanning electron microscopy.[9] However, the fracture faces of such SLS outlet struts cannot be imaged without sectioning the struts, which would prevent further evaluation of the spatial relations between the strut and other valve components. Imaging of the fracture faces of a group of OSF outlet struts by optical and scanning electron microscopy to conduct fractographic examinations has been reported.[5] The fractographic observations include striations indicating fatigue failure, and fracture initiation sites were identified on inflow sides only, commonly in the weld but sometimes in the heat-affected (near-weld) zone or the base metal. Other methods like X-ray micro-computed tomography (micro-CT) were used to obtain accurate, high-resolution three-dimensional (3-D) images of small objects.[31] The micro-CT imaging modality was used to characterize non-destructively the morphology and position of fractures in the outlet struts of SLS-BSCC valve in vitro.[31] This approach was pursued because CT is superior to regular projection X-ray imaging for several reasons.[31] One is that projection along one axis may be unable to detect a generally planar crack or fracture when fracture faces are nearly in contact, since the radio density along any one projection axis may be nearly constant. Moreover, even if a fracture is detected with projection X-ray imaging, no information on 3-D features of the fracture faces, such as fatigue striations, or wear burnishing, can be obtained. Furthermore, an accurate measurement of the distances separating the fracture faces can best be obtained from a high-resolution 3-D image as provided by micro-CT. Although, the application of micro-CT to image outlet strut fractures in BSCC valves explants demonstrates the value of this method for fracture characterization in vitro, including visualization of the fracture faces of the SLS struts without physical sectioning. Consequently, this method is not suitable for clinical use, because it requires high-intensity, dangerous X-ray radiation. Micro-CT can serve as a tool to understand the failure mechanisms, and perhaps to aid in the development of clinical differentiation methods.[31]

SUMMARY OF THE PRESENT INVENTION

The present invention is a non-invasive method and apparatus to determine the structural integrity of an implanted BSCC by insonifying the implanted heart valve with a megahertz frequency to cause the structural components of the heart valve to vibrate and a lower kilohertz frequency to cause the individual structural components of the heart valve being investigated to vibrate at their resonant frequency. From experimental testing, the present inventors have established resonant frequency ranges of certain structural components of the BSCC valve which indicate that at certain resonant frequency ranges the heart valve components are intact. At other resonant frequency ranges, certain components are in danger of breaking. At other frequency ranges, the components of the heart valve are broken. Through the present invention, the condition of the BSCC can be determined in order to provide a clinical determination as to whether or not the implanted BSCC needs to be replaced.

It has been discovered, according to the present invention, that the defect in the BSCC which resulted in the heart valve failure in patients was due to a manufacturing defect in the BSCC rather than the inherent design of the BSCC. Referring to the BSCC illustrated in FIG. 1, both the outlet strut 2 and the inlet strut 4 do not move. The occluder disc 3 moves as it is retained between the inlet strut 4 and outlet strut 2. As the flow of blood runs through the disc 3, longitudinal forces are created on the disc 3 and there is also a torsional impact on the disk 3 which may cause the disc 3 to rotate. The torsional force combined with the opening and closing of the disk based upon the cycling of the heart creates an impact on the end of the outlet strut 2 which is then transmitted to the legs of the outlet strut. It has been discovered that the manufacturing defect was created when the leg of the outlet strut 2 was welded to the housing ring 1. After the heat of welding, the ring 1 and outlet strut 2 were rapidly cooled down and this created a void at the intersection of the weld of the strut 2 of the ring 1. The above described forces impacted the location of the void and led to development of cracks and ultimate separation of a strut leg from the ring 1. If both strut legs were separated from the ring 1, the valve fails because the disc is swept away since the outlet strut 2 which served to assist in retaining the disc 3 could no longer do so.

It has further been discovered, according to the present invention, that the inherent defect combined with the forces at the location of the strut legs and ring can create two types of fractures. One is called a kissing fracture where there the two ends of the fractured leg of the outlet strut 2 (whether at the welding site to the ring 1 or adjacent to the welding site with the ring 1) are in contact. The other condition is where the two ends of the fractured leg (whether at the welding site to the ring 1 or adjacent to the welding site with the ring 1) are completely separated (called a separated fracture). For a separated fracture, the two ends of the fracture do not touch each other.

It has been discovered, according to the present invention, that if the resonant frequency of the BSCC outlet strut is in the range of 6.5 KHz to 12 KHz with a preferred median of about 7 KHz, then the outlet strut is intact. If the resonant frequency of the BSCC outlet strut is in the range of 3.6 KHz to 4.5 KHz with a preferred median of about 4 KHz, then the BSCC may have a kissing fracture. If the resonant frequency of the BSCC outlet strut is in the range of 1.9 KHz to 2.4 KHz, the two ends of the fracture are separated and at least one outlet strut leg has become weakened.

It has additionally been discovered, according to the present invention, that in order to cause a component of the BSCC valve to vibrate at its resonant frequency to determine its condition, the component of the valve or the valve in its entirety must be energized or insonified. The acoustic pressure is induced to the valve by a megahertz frequency. The megahertz frequency is accompanied with another megahertz frequency superimposed by a kilohertz frequency creating a delta frequency in the kilohertz range that corresponds with the resonant frequency of the specific component of interest and which sets the specific component of the BSCC valve to vibrate at its resonant frequency in order to determine its structural condition.

More specifically, it has been discovered, according to the present invention, that in order to cause the outlet of the BSCC valve to vibrate at its resonant frequency in order to determine its condition, the BSCC valve must be impacted with a megahertz frequency in the 1 MHz to 10 MHz in order to deliver sound energy or acoustic pressure to the BSCC valve and thereafter, the BSCC heart valve must be insonified with the modulated and interrogating frequency in the range of 1 KHz to 12 KHz in order to induce the outlet strut component of the BSCC heart valve to vibrate at its natural or resonant frequency. Thereafter, the present invention measures the emitted kilohertz resonant frequency of the BSCC valve outlet strut with frequency detection means and comparing the recorded resonant frequency to predetermine categories of resonant frequencies in order to determine if the legs of the outlet strut are intact or if at least one leg of the outlet strut at a location adjacent to or at the welding site where the at least one leg is welded to the orifice ring has sustained a kissing fracture or has sustained a separated fracture.

It has been further discovered that one method of achieving the insonification is achieved by using two separate single focused transducers with a first transducer generating a megahertz frequency in the range of 1 MHz to 10 MHz and a second transducer generating a megahertz frequency in the range of 1 MHz to 10 MHz and having superimposed thereon a kilohertz frequency in the range of 1 KHz to 12 KHz with both transducers focusing on the BSCC heart valve outlet strut. In this method, the resonant frequency generated by and as emitted from the BSCC heart valve outlet strut is measured by an acoustic detector having a wide angle of acoustic acceptance, high sensitivity, high dynamic range and a flat response in the range of 1 Hz to 20 KHz.

It has also been discovered, according to the present invention, that another method for achieving the insonification is by using a confocal sectionalized dual element transducer having two sections, a first section providing a megahertz frequency in the range of 1 MHz to 10 MHz and a second section providing megahertz frequency in the range of 1 MHz to 10 MHz and having superimposed thereon, a kilohertz frequency in the range of 1 KHz to 12 KHz, with both sections focusing the generated frequencies on the BSCC heart valve outlet strut. For this embodiment, the resonant frequency generated by and emitted from the BSCC valve outlet strut is measured by an acoustic detector having a wide angle of acoustic acceptance, high sensitivity, high dynamic range and a flat response in the range of 100 to 20 KHz.

It has also been discovered, according to the present invention, that a third method for achieving the insonification is by using a single element non-focused transducer in which an input driving voltage that activates the transducer is amplitude modulated to insonify the BSCC valve. Such amplitude modulated signal carries a center frequency in the range of 1 MHz to 10 MHz and an amplitude modulated low frequency in the range of 1 KHz to 12 KHz with the amplitude modulated signal being aimed at the BSCC heart valve. For this method, the resonant frequency generated by and emitted from the BSCC outlet strut is measured by an acoustic detector having a wide angle of acoustic acceptance, high sensitivity, high dynamic range and a flat response in the range of 1 Hz to 20 KHz.

It has further been discovered, according to the present invention, that the integrity of at least one leg of the outlet strut is determined to be intact, having sustained a kissing fracture or having sustained a separated fracture by generating any combination or subtraction of frequencies that can set the outlet strut to vibrate at its natural resonant frequency.

It has further been discovered, according to the present invention, that since the BSCC heart valve opens and closes during a cardiac cycle, it is preferred to have the interrogation and resonant frequency detection performed only at the instant and time when the BSCC heart valve is closed.

It has further been discovered, according to the present invention, that in the preferred embodiment, since the BSCC heart valve opens and closes during a cardiac cycle, it is preferred to have the interrogation and resonant frequency-detection performed during the cardiac cycle after the heart valve is closed and before the heart valve reopens.

It has further been discovered, according to the present invention, that if a hydrophone is used to detect the kilohertz frequency of the resonating BSCC, then the resonant frequency of the BSCC valve components can be determined in order to determine the structural condition of the BSCC.

It is therefore a primary object of the present invention to generate an insonification and integrity frequency to cause the implanted BSCC valve to vibrate and cause the components of the BSCC to vibrate at their resonant frequency so that the condition of the components, and in particular the attachment of the legs of the outlet strut to the housing ring can be determined.

It is also an object of the present invention to provide a non-invasive method and apparatus to determine the condition of an implanted BSCC valve by non-invasive active acoustic means wherein the BSCC valve is caused to vibrate at its resonant frequency so that the condition of the implanted BSCC can be determined.

Described broadly, it is an object of the present invention to provide a non-invasive method to identify the structural integrity of components of the Bjork Shiley Convexo-Concave (BSCC) heart valve which comprises, impacting the BSCC heart valve with a megahertz frequency in the range of 1 MHz to 10 MHz in order to deliver sound energy or acoustic pressure to the BSCC heart valve; insonifying the BSCC heart valve with a modulated and interrogating frequency in the range of 1 KHz to 50 KHz in order to induce the structural components of the BSCC heart valve to vibrate at their resonant frequencies; and measuring the emitted kilohertz resonant frequencies of the BCSS heart valve structural components with frequency detection means to determine the resonant frequencies at which the structural components of the BSCC heart valve are vibrating and comparing the resonant frequencies to predetermined categories of resonant frequencies in order to determine if the structural components are intact or have sustained fractures.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DETAILED DESCRIPTION OF THE PREFERRED EMBODIMENT

Figure 1:
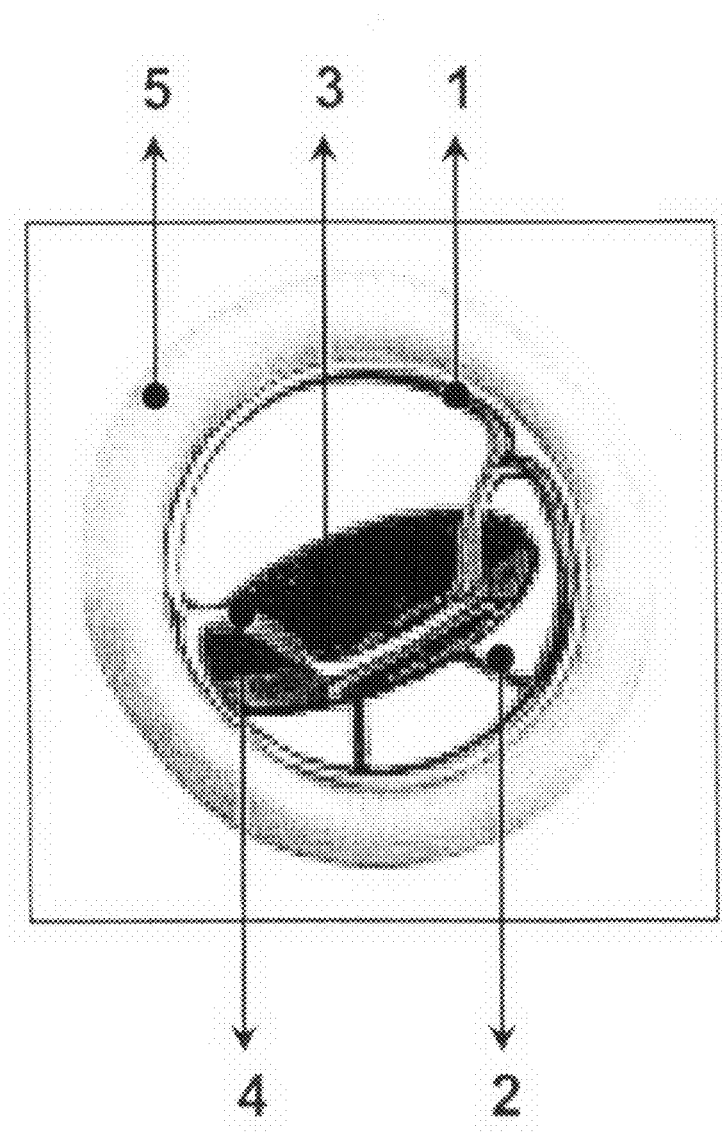
FIG. 1 is a perspective view of component of a Bjork Shiley Convexo-Concave Mechanical Heart Valve.

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within th spirit, scope and contemplation of the present invention as further defined in the appended claims.

The present invention is a procedure for the noninvasive diagnosis of the integrity of such implants where current modern imaging technologies and other classifiers are either unable to provide reliable evaluation or such evaluation involves costly complications. The case of BSCC heart valves is (1) complicated, due to the dynamic and transient nature of cardiac pulsation and (2) time-sensitive, because any failure of these flow-regulating passive devices will present life-threatening consequences.

The present invention is based on the utilization of noninvasive remote ultrasound radiation for the low frequency, acoustic stimulation of the implants, to determine the possible existence of faults by measuring their acoustic signatures and comparing with the signature of intact outlet strut. Generally, it is well known in the art that many mechanical structures, especially those characterized by distinguished vibratory shapes and materials, manifest acoustic natural resonances at particular frequencies, which can serve as their acoustic signatures.[22, 23] The classical example is the tuning fork, which serves as a standard calibration frequency for musicians and other applications. The acoustic signature is strongly dependent on the structure, material strain coefficients and the submerging environment of the implants.[18-21] These resonances can be experimentally measured by the excitation of the modes of vibrations and listening to the radiated acoustic waves by known listening instrumentations, like our ears, microphones, accelerometers, etc. Additionally, such acoustic resonances can be theoretically predicted using different computer programs, like the Finite Elements Method.[30] It is also well known in the art that some of these acoustic signatures will dramatically change on the introduction of faults (fractures, voids, loss of elasticity, etc.) in the structures. These changes will be manifested as changes in the acoustic resonance frequencies. This is usually caused by the fact that such faults will, in many cases, distinctively affect the acoustic wave propagation inside the object. Consequently, the acoustic signatures will change to represent the new effective faulted structure. Present invention remotely measures the characteristic acoustic signature of the implant, using high frequency (MHz) ultrasound radiation, which is well known to be able to penetrate the human body and focus on the interrogated objects with high resolution and precision.[24-29] For internally installed artificial implants there is great difficulty to directly aim tow frequency acoustic radiation, to measure the characteristic resonance spectrum of these structures. Consequently, the resulting wavelength for the above-mentioned low frequency insonification is around 15 m to 7.5 cm, respectively. Such long acoustic waves prevent their direct noninvasive remote stimulation of the implants, to measure the implants' characteristic acoustic frequencies, which can lead to the identification of developing dangerous faults. However, ultrasound radiation modalities have a much smaller wavelength, to demonstrate the necessary spatial resolution for exact targeting of the interrogated implant.

1.1 Ultrasound Based Noninvasive Remote Medical Diagnosis

Figure 2:
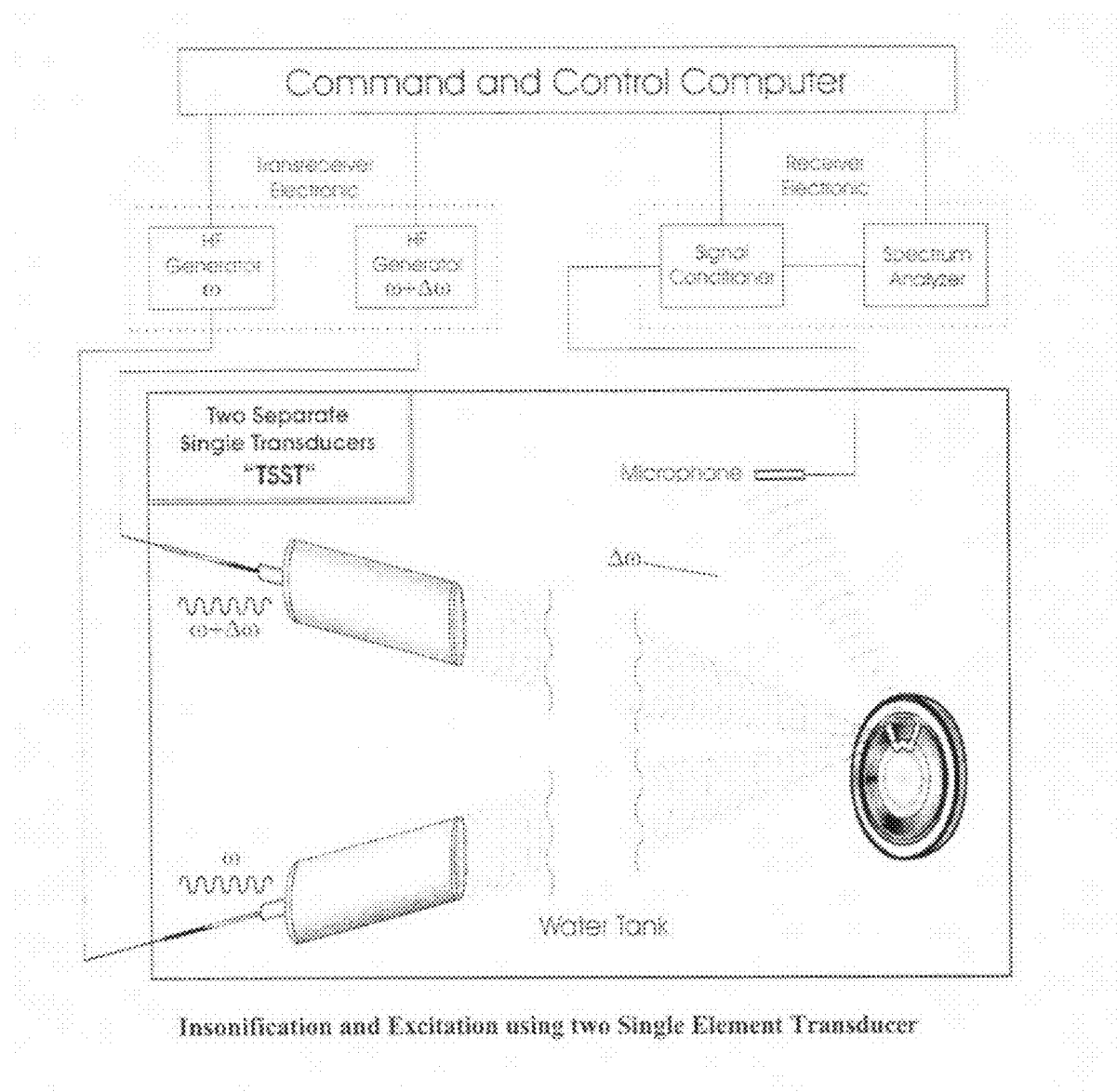
FIG. 2 is a schematic and block diagram of one method of the present invention utilizing two separate single element focused transducers with frequencies aimed at the same point.
Figure 3:
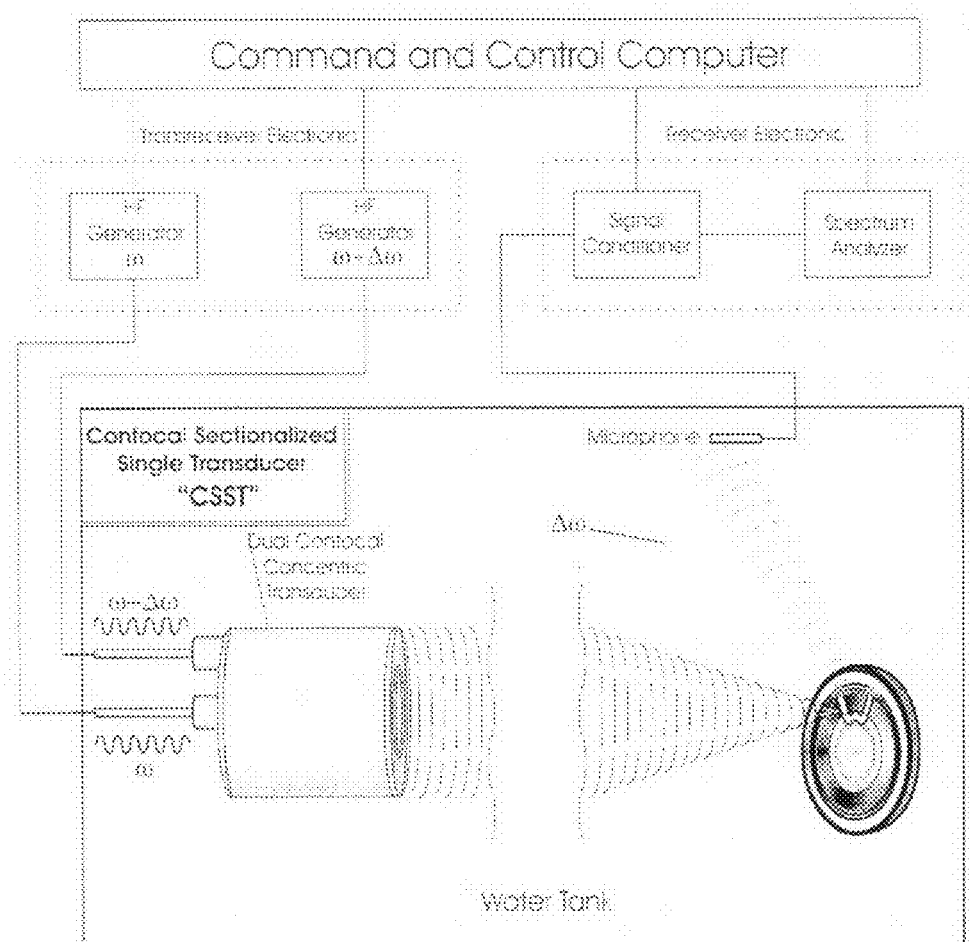
FIG. 3 is a schematic and block diagram of an alternative method of the present invention using one confocal sectionalized single element focused transducer with each section separately providing the insonification frequency aimed at the same point.
Figure 4:
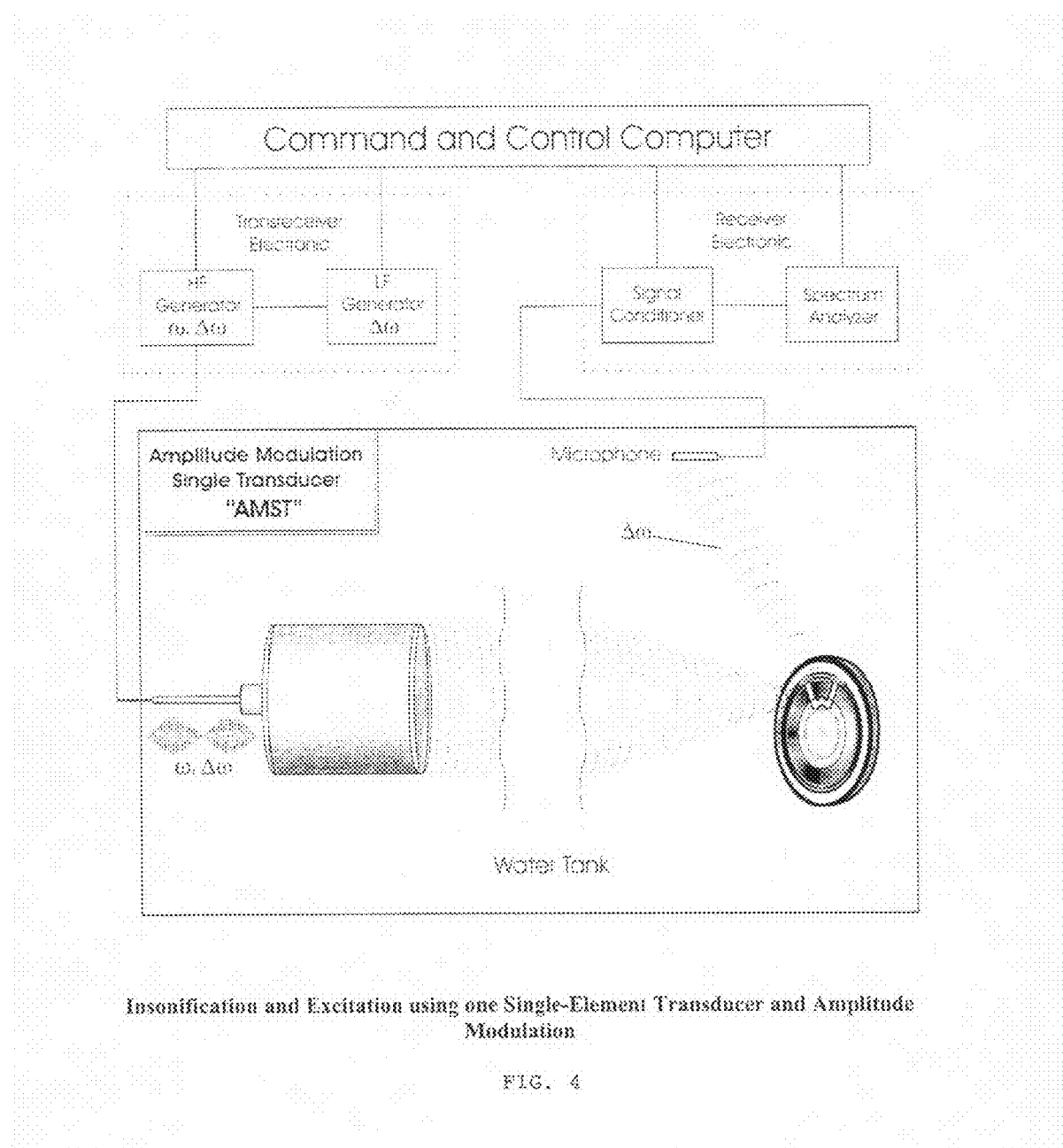
FIG. 4 is a schematic and block diagram of an alternative method of the present invention using a single element transducer in which the input driving voltage that activates the transducer is amplitude-modulated to insonify high frequency amplitude modulation with carrier megahertz frequency and kilohertz frequency amplitude modulation.

The invention for the noninvasive remote diagnosis of the implants' health is based on the insonification of the implant with two ultrasound radiation waves differing slightly in frequency, to result in a low frequency force, at the implant. This low frequency radiation force will stimulate the implant and instigate its vibration.[24-26a,b] The response of the implant which is related to the difference of the two transmitted frequencies (low frequency modulation), is measured by a noninvasive remote low frequency (kHz) acoustic detector. This measurement allows the evaluation of the acoustic signatures, thus providing information on the implant's structural integrity. The low frequency noninvasive detector can be comprised of a microphone, hydrophone or an accelerometer. FIGS. 2-4 describe the schematics of a few versions of the invention, meant for the noninvasive remote diagnosis of the structural integrity of implants. This technique is involves two main components:

(i) The aiming high frequency ultrasound insonifiers and
(ii) The wide angle, low frequency acoustic detector 1.2 The High Frequency Ultrasound Insonifiers The high frequency ultrasound insonification subsystem (transducer), remotely aims at the implant to be interrogated, to simultaneously provide an acoustic interference at the implant. The interference will result on the implant, a low frequency radiation force at frequency equal to the difference in the two transmitted ultrasound waves. The transducer provides an interference of two ultrasound frequencies $W_0$ and W, to provide a low frequency radiation force with a frequency $\Delta W=W-W_0$ at the implant. The low frequency $\Delta W$ is scanned to detect the specific acoustic signature of the particular implant (i.e. outlet strut). If the $\Delta W$ generated by the transducer matches with the acoustic signature of the implant, then the target starts to vibrate at that frequency and generates an acoustic response which can be detected by a tow frequency detector explained in the following section. The transducer is manually adjusted so that the ultrasound force is incident at the right spot either on the target or on the immediate vicinity of the target so as to maximize the response of the implant The generation of the low frequency difference force can be achieved by three different means which can be equally used to insonify the target in order to detect the its characteristic signatures.

These are:

(i) Two separate single element (crystal) transducers with frequencies $W_0$ and $W=W_0+\Delta W$ aiming at the same point. This system is shown schematically in FIG. 2. For this method as disclosed in FIG. 2, insonification is achieved by using two separate single focused transducers with a first transducer generating a megahertz frequency in the range of 1 MHz to 10 MHz and a second transducer generating a megahertz frequency in the range of 1 MHz to 10 MHz and having superimposed thereon a kilohertz frequency in the range of 1 KHz to 12 KHz, with both transducers focusing on the BSCC heart valve outlet strut. Alternatively, the superimposed frequency can be in the range of 1 KHz to 50 KHz.

(ii) A confocal sectionalized single element transducer, each section providing separately the insonification at W and Wo, respectively. This confocal single transducer insonification is shown schematically in FIG. 3. For the embodiment as shown in FIG. 3, the insonification is achieved by using a confocal sectionalized dual element transducer having two sections, a first section providing a megahertz frequency in the range of 1 MHz to 10 MHz and a second section providing megahertz frequency in the range of 1 MHz to 10 MHz and having superimposed thereon a kilohertz frequency in the range of 1 KHz to 12 KHz, with both sections focusing the generated frequencies on the BSCC heart valve outlet strut. Alternatively, the superimposed frequency can be in the range of 1 KHz to 50 KHz.

(iii) A single element transducer in which the input driving voltage that activates the transducer, is amplitude-modulated (AM), to insonify high frequency AM modulation, with carrier frequency Wo and low frequency amplitude modulation AW, which is equivalent to the radiation at Wi. $W_0-\Delta W$, and $W_2=W_0+\Delta W$. This is shown schematically in FIG. 4.

For the embodiment as illustrated in FIG. 4, insonification is achieved by using a single element non-focused transducer in which an input driving voltage that activates the transducer is amplitude modulated to insonify high frequency amplitude modulation with a carrier frequency in the range of 1 MHz to 10 MHz and an amplitude modulated low frequency in the range of 1 KHz to 12 KHz with the amplitude modulated signals being aimed at the BSCC heart valve. Alternatively, the amplitude modulated low frequency can be in the range of 1 KHz to 50 KHz.

For each of these methods, the acoustic detector can have a wide angle of acoustic acceptance, high sensitivity, high dynamic range and a flat response in the range of 1 Hz to 20 Hz.

Each of these three different ultrasound high frequency sources applies a low frequency component of the radiation force at the implant, to allow the stimulation of the implant resonances. In the first two techniques, the down conversion to low frequency occurs only at the two beams' mutual intersection. However, in the third case, based on electronic generation of the modulated ultrasound radiation at the transducer, the low frequency AW occurs all along the propagating beam path. This may allow possible acoustic stimulation of many unrelated elements along the way, which can contribute to noise background, as well as to false observations. Since, the low frequency force is present all along the path of the transmitted ultrasonic beam, any object that lies in this path will start to vibrate and give incorrect peaks or erroneous results (noise or artifacts).

1.3 The Wide Angle, Low Frequency Acoustic Detector

The low frequency radiation force produced by the high frequency ultrasound transducer stimulated the implant, which in turn vibrates at its resonant frequency and emits a radial acoustic field. This acoustic response is characteristic signature of each implant and is different for each class of the valve. This response is detected by an acoustic detector like a microphone, hydrophone, accelerometer etc. The detector has to have adequate sensitivity to collect the response of the implant with a high dynamic range. The detectors used in our case were sensitive hydrophones and accelerometers. It is always preferable to have a detector that has a wide angle of acceptance (or omni-directional), high sensitivity, high dynamic range, flat response in the range of 10 Hz to 20 KHz.

2. The Reduction of the Invention to Practice 2.1 Experiments with the BSCC Heart Valve The current invention was reduced to practice by the successful demonstration of noninvasive remote diagnosis of the health of struts in the Bjork-Shiley Convexo-Concave (BSCC) mechanical heart valves (FIG. 1). The structural condition of the outlet strut is crucial for the functionality of the BSCC heart valve, as the development of faults in the struts can be life-threatening. Consequently, it is of high importance to be able to diagnose the health of the struts on a routine basis without the need of surgery. As mentioned before, all the current imaging techniques have failed to classify the condition of the outlet crucial struts. Our resonance recognition experiments were conducted on an assembly of 75 BSCC intact and fractured valves, some of which were explants. The valves exhibited different fracture conditions, in which a through fracture was developed in the outlet (Single Leg Separation (SLS)). The BSCC valves of different standard sizes (23-33) mm body dimensions, were pre-examined under an optical microscope and a scanning electron microscope (SEM), to reveal the nature of the SLS faults. Accordingly, the valves were divided into three different groups:

(i) Group BSCC-INT Intact BSCC valves.

(ii) Group BSCC-SLS-NG: BSCC valves with SLS without a gap.

(iii) Group BSCC-SLS-G: BSCC valves with SLS and a gap.

The experiments were conducted in water, where all the components were immersed, thereby mimicking the human soft tissue, which has ultrasonic impedance and sound velocity close to water. In all cases the insonifying transducer(s) were about 75 mm away from the interrogated BSCC valve, while aiming at the strut location or at its vicinity. The distance of 75 mm was selected to mimic an average distance between the heart valve and the available exterior ultrasound window between the ribs on the chest wall. Hydrophones and accelerometer were used as sensors to detect the response of the stimulated implant. The hydrophone was located to the side of the tested valve, while avoiding the high-frequency ultrasound radiation path.

In principle, all of the three insonification methods induce radiation forces of low frequencies on the strut to stimulate its low frequency spectrum, which allow the measurement of the acoustic signature. Due the complex nature and problems involved in focusing, the first technique is not preferred for experimentation. The ultrasound carrier frequency used, is between 1 MHz and 10 MHz, with a typical center frequency at 3 MHz. This induces acoustic waves in water with wavelength of about 500 um. The low frequency modulation was scanned in the range 1.0 KHz $\Delta W$ s 10.0 KHz. Typical transducers had a diameter of about 25 mm, with a dual confocal equivalent concentric configuration, and also a single element transducer of 18.75 mm diameter. However, many others, focused and unfocused transducers with different configurations, were used in order to optimize the low frequency radiation forces on different interrogated targets. Recording sensors used were high sensitivity, low noise hydrophones. In some cases BSCC valves were mounted on a waterproof accelerometer for direct measurement of vibration induced by the low frequency radiation. The synchronous hydrophone signals were filtered and conditioned and spectrally analyzed. The experiments distinctively reveal that the faulted valves manifest lower acoustic signature frequencies higher relative intensities than the intact valve signatures.

The experiments clearly revealed that the fractured valves manifest distinguished acoustic signatures different than intact valves. Whereas, the BSCC valves with intact struts (Group BSCC-IT) all demonstrate resonances near 7 KHz, the two groups of BSCC valves with the fractured outlet struts exhibit lower acoustic frequency resonances. The group BSCC-SLS-NG in which the outlet struts manifest SLS without a gap resulted in resonance frequencies around 4 KHz, whereas the group BSCC-SLS-G in which the fracture ends are separated (gap) demonstrated frequencies around 2 KHz. Consequently, the acoustic frequency as measured by the invented methodology was able to reliably differentiate between the fractured BSCC valves and the intact valves.

The above experiments confirm that in order to cause the components of the BSCC to vibrate at a resonant frequency in order to determine the condition of the BSCC, the BSCC must be impacted with a megahertz frequency in the 1 MHz to 10 MHz in order to deliver sound energy or acoustic pressure to the BSCC heart valve and thereafter, the BSCC heart valve must be insonified with the modulated and interrogating frequency in the range of 1 KHz to 12 KHz in order to induce the outlet strut component of the BSCC heart valve to vibrate at its natural or resonant frequency. Thereafter, the present invention measures the emitted KHz frequency of the BSCC heart valve outlet struts with frequency detection means to determine the resonant frequency at which the outlet strut of the BSCC heart valve is vibrating and comparing the resonant frequency to predetermine categories of resonant frequencies in order to determine if the legs of the outlet strut at the location adjacent to the attachment sites where the legs are welded to the orifice ring are intact or if at least one leg of the outlet strut at a location adjacent to or at the welding site where the at least one leg is welded to the orifice ring has sustained a kissing fracture or has sustained a separated fracture.

The above experiments also confirm that one method of achieving the insonification is achieved by using two separate single focal transducers with a first transducer generating a megahertz frequency in the range of 1 MHz to 10 MHz and a second transducer generating a megahertz frequency in the range of 1 MHz to 10 MHz and having superimposed thereon a kilohertz frequency in the range of 1 KHz to 12 KHz with both transducers focusing on the BSCC heart valve outlet strut. In this method, the resonant frequency generated by the BSCC heart valve outlet strut is measured by an acoustic detector having a wide angle of acoustic acceptance, high sensitivity, high dynamic range and a flat response in the range of 1 Hz to 20 KHz.

The above experiments also confirm that another method for achieving the insonification is by using a confocal sectionalized dual element transducer having two sections, a first section providing a megahertz frequency in the range of 1 MHz to 10 MHz and a second section providing megahertz frequency in the range of 1 MHz to 10 MHz and having superimposed thereon, a kilohertz frequency in the range of 1 KHz to 12 KHz, with both sections focusing the generated frequencies on the BSCC heart valve outlet strut. For this embodiment, the resonant frequency generated by the BSCC heart valve outlet strut is measured by an acoustic detector having a wide angle of acoustic acceptance, high sensitivity, high dynamic range and a flat response in the range of 100 to 20 KHz.

The above experiments also confirm that a third method for achieving the insonification is by using a single element non-focused transducer in which an input driving voltage that activates the transducer is amplitude modulated to insonify high frequency amplitude modulations where they carry a frequency in the range of 1 MHz to 10 MHz and an amplitude modulated low frequency in the range of 1 KHz to 12 KHz with the amplitude modulated signals being aimed at the BSCC heart valve. For this method, the resonant frequency generated by the BSCC outlet strut is measured by an acoustic detector having a wide angle of acoustic acceptance, high sensitivity, high dynamic range and a flat response in the range of 1 Hz to 20 KHz.

The above experiments also confirm that the integrity of at least one leg of an outlet strut is determined to be intact, having sustained a kissing fracture or having sustained a separated fracture by generating any combination or subtraction of frequencies that can set the outlet strut to vibrate at its natural resonant frequencies.

The above experiments also confirm that since the BSCC heart valve opens and closes during a cardiac cycle, it is preferred to have the interrogation and resonant frequency detection performed only at the instant and time when the BSCC heart valve is closed.

The above experiments also confirm that in the preferred embodiment, since the BSCC heart valve opens and closes during a cardiac cycle, it is preferred to have the interrogation and resonant frequency detection performed during the cardiac cycle after the heart valve is closed and before the heart valve reopens.

The above experiments also confirm that if a hydrophone is used to detect the kilohertz frequency of the resonating BSCC, then the resonant frequency of the BSCC components can be determined in order to determine the condition of the BSCC.

In conclusion, the results demonstrate conclusively that the resonant frequency signatures of the BSCC valves as measured by the invented methodology can reliably determine the structural integrity of the BSCC heart valves.

Described in detail the present invention is a non-invasive method to identify the structural integrity of legs of an outlet strut attached to an orifice ring of a Bjork Shiley Convexo-Concave (BSCC) heart valve implanted in a human, comprising: (a) impacting the BSCC heart valve with a megahertz frequency in the range of 1 MHz to 10 MHz in order to deliver sound energy or acoustic pressure to the BSCC heart valve; (b) insonifying the BSCC heart valve with a modulated and interrogating frequency in the range of 1 KHz to 12 KHz in order to induce the outlet strut component of the BSCC heart valve to vibrate at its natural or resonant frequency; and (c) measuring the emitted kilohertz resonant frequency of the BCSS heart valve outlet strut with frequency detection means to determine the resonant frequency at which the outlet strut of the BSCC heart valve is vibrating and comparing the resonant frequency to predetermined categories of resonant frequencies in order to determine if the legs of the outlet strut at the locations adjacent to or at the attachment sites where the legs are welded attached to the orifice ring are intact or if at least one leg of the outlet strut at a location adjacent to or at the welding site where the at least one leg is welded to the orifice ring has sustained a kissing fracture or has sustained a separated fracture.

Described alternatively and more broadly invention is a non-invasive method to identify the structural integrity of structural components of a Bjork Shiley Convexo-Concave (BSCC) heart valve implanted in a human, comprising: (a) impacting the BSCC heart valve with a megahertz frequency in the range of 1 MHz to 10 MHz in order to deliver sound energy or acoustic pressure to the BSCC heart valve; (b) insonifying the BSCC heart valve with a modulated and interrogating frequency in the range of 1 KHz to 50 KHz in order to induce the structural components of the BSCC heart valve to vibrate at their resonant frequencies; and (c) measuring the emitted kilohertz resonant frequencies of the BCSS heart valve structural components with frequency detection means to determine the resonant frequencies at which the structural components of the BSCC heart valve are vibrating and comparing the resonant frequencies to predetermined categories of resonant frequencies in order to determine if the structural components are intact, have sustained a kissing fracture or have sustained a separated fracture.

Described alternatively broadly, the present invention is a non-invasive method to identify the structural integrity of legs of an outlet strut attached to an orifice ring of a Bjork Shiley Convexo-Concave (BSCC) heart valve implanted in a human, comprising: (a) impacting the BSCC heart valve with a megahertz frequency sufficient to deliver sound energy or acoustic pressure to the BSCC heart valve; (b) insonifying the BSCC heart valve with a modulated and interrogating kilohertz frequency in order to induce the outlet strut component of the BSCC heart valve to vibrate at its resonant frequency; and (c) measuring the emitted kilohertz resonant frequency of the BCSS heart valve outlet strut with frequency detection means to determine the resonant frequency at which the outlet strut of the BSCC heart valve is vibrating and comparing the resonant frequency to predetermined categories of resonant frequencies in order to determine if the legs of the outlet strut at the locations adjacent to or at the welding sites where the legs are attached to the orifice ring are intact or if at least one leg of the outlet strut at a location adjacent to or at the welding site where the at least one leg is welded to the orifice ring has sustained a kissing fracture or has sustained a separated fracture.

Defined more broadly, the present invention is a A non-invasive method to identify the structural integrity of at least one structural component of a Bjork Shiley Convexo-Concave (BSCC) heart valve implanted in a human, comprising: (a) impacting the BSCC heart valve with a megahertz frequency sufficient to deliver sound energy or acoustic pressure to the BSCC heart valve; (b) insonifying the BSCC heart valve with a modulated interrogating kilohertz frequency in order to induce the at least one structural component of the BSCC heart valve to vibrate at its resonant frequency; and (c) measuring the emitted kilohertz resonant frequency of the BCSS heart valve at least one structural component with frequency detection means to determine the resonant frequency at which the at least one structural component of the BSCC heart valve is vibrating and comparing the resonant frequency to predetermined categories of resonant frequencies in order to determine if the at least one structural component is intact, has sustained a kissing fracture or has sustained a separated fracture.

Defined most broadly, the present invention is a A non-invasive method to identify the structural integrity of at least one structural component of a Bjork Shiley Convexo-Concave (BSCC) heart valve implanted in a human, comprising: (a) delivering energy to the BSCC heart valve and insonifying the BSCC heart valve with a frequency in order to induce the at least one structural component of the BSCC heart valve to vibrate at its resonant frequency; and (b) measuring the emitted resonant frequency of the BCSS heart valve at least one structural component with frequency detection means to determine the resonant frequency at which the at least one structural component of the BSCC heart valve is vibrating and comparing the resonant frequency to predetermined categories of resonant frequencies in order to determine if the at least one structural component is intact, has sustained a kissing fracture or has sustained a separated fracture.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which the invention might be embodied or operated.

What is claimed is:

1. A non-invasive method to identify the structural integrity of each of two legs of an outlet strut welded attached to an orifice ring of a Bjork Shiley Convexo-Concave (BSCC) heart valve implanted in a human, comprising:
    a. having the outlet strut having two legs which are each welded attached to the orifice ring of the Bjork Shiley Convexo-Concave heart valve, impacting the BSCC heart valve with a megahertz frequency in a range of 1 MHz to 10 MHz in order to deliver sound energy or acoustic pressure to the BSCC heart valve;
    b. insonifying the BSCC heart valve with a modulated and interrogating frequency in the range of 1 KHz to 12 KHz in order to induce the outlet strut component of the BSCC heart valve to vibrate at its natural or resonant frequency to thereby emit a kilohertz resonant frequency of the outlet strut of the BCSS heart valve in the same kilohertz frequency range; and
    c. detecting the emitted kilohertz resonant frequency of the BCSS heart valve outlet strut with a frequency detection member to determine the resonant frequency at which the outlet strut of the BSCC heart valve is vibrating and analyzing all the resonant frequencies in order to determine if the legs of the outlet strut at the locations adjacent to or at the attachment sites where the legs are welded attached to the orifice ring are intact or if at least one leg of the outlet strut at a location adjacent to or at the welding site where the at least one leg is welded to the orifice ring has sustained a kissing fracture or has sustained a separated fracture.

2. The method in accordance with claim 1 wherein the interrogating frequencies to determine the integrity of the legs of the outlet strut cause a response frequency which is in the range of 6.5 KHz to 12 KHz if the legs of the outlet strut are intact, in the range of 3.6 KHz to 4.5 KHz if at least one leg of the outlet strut has sustained a kissing fracture, and in the range of 1.9 KHz to 2.4 KHz if at least one leg of the outlet strut has sustained a separated fracture.

3. The method in accordance with claim 1 wherein the insonifying and impacting are achieved by using two separate single focused transducers with a first transducer generating a megahertz frequency in the range of 1 MHz to 10 MHz and a second transducer generating a megahertz frequency in the range of 1 MHz to 10 MHz and having superimposed thereon a kilohertz frequency in the range of 1 KHz to 12 KHz, with both transducers focusing on the BSCC heart valve outlet strut.

4. The method in accordance with claim 3 wherein the resonant frequency emitted by the BSCC heart valve outlet strut is detected by an acoustic detector having a wide angle of acoustic acceptance, high sensitivity, high dynamic range and a flat response in the range of 1 Hz to 20 KHz.

5. The method in accordance with claim 1 wherein the insonifying and impacting are achieved by using a confocal sectionalized dual element transducer having two sections, a first section providing a megahertz frequency in the range of 1 MHz to 10 MHz and a second section providing megahertz frequency in the range of 1 MHz to 10 MHz and having superimposed thereon a kilohertz frequency in the range of 1 KHz to 12 KHz, with both sections focusing the generated frequencies on the BSCC heart valve outlet strut.

6. The method in accordance with claim 5 wherein the resonant frequency emitted by the BSCC heart valve outlet strut is detected by an acoustic detector having a wide angle of acoustic acceptance, high sensitivity, high dynamic range and a flat response in the range of 1 Hz to 20 KHz.

7. The method in accordance with claim 1 wherein the insonifying and impacting are achieved by using a single element non-focused transducer in which an input driving voltage that activates the transducer is amplitude modulated to insonify high frequency amplitude modulation with a carrier frequency in the range of 1 MHz to 10 MHz and an amplitude modulated low frequency in the range of 1 KHz to 12 KHz with the amplitude modulated signals being aimed at the BSCC heart valve.

8. The method in accordance with claim 7 wherein the resonant frequency emitted by the BSCC outlet strut is detected by an acoustic detector having a wide angle of acoustic acceptance, high sensitivity, high dynamic range and a flat response in the range of 1 Hz to 20 KHz.

9. The method in accordance with claim 1 wherein the integrity of at least one leg of an outlet strut is determined to be intact, to have sustained a kissing fracture or to have sustained a separated fracture, by generating any combination or subtraction of frequencies that cause the outlet strut to vibrate at its natural resonant frequencies.

10. The method in accordance with claim 1 wherein the BSCC heart valve opens and closes during a cardiac cycle and the interrogation and resonant frequency detection are performed only at the instant in time when the BSCC heart valve is closed.

11. The method in accordance with claim 1 further comprising the BSCC heart valve opens and closes during a cardiac cycle and an interrogation and resonant frequency detection are performed during the cardiac cycle after the heart valve is closed and before the heart valve reopens.

12. A non-invasive method to identify the structural integrity of structural components of a Bjork Shiley Convexo-Concave (BSCC) heart valve implanted in a human, comprising:
    a. impacting the BSCC heart valve with an ultrasonic megahertz frequency in the range of 1 MHz to 10 MHz in order to deliver sound energy or acoustic pressure to the BSCC heart valve;

b. insonifying the BSCC heart valve with a swept modulated and interrogating frequency in the range of 1 KHz to 50 KHz in order to induce the structural components of the BSCC heart valve to vibrate at their resonant frequencies; and
c. detecting the emitted kilohertz resonant frequencies of the BCSS heart valve structural components with a frequency detection member to determine all resonant frequencies at which the structural components of the BSCC heart valve are vibrating and the analyzing all resonant frequencies in order to determine if the structural components are intact, have sustained a kissing fracture or have sustained a separated fracture.

13. The method in accordance with claim 12 further comprising the BSCC heart valve opens and closes during a cardiac cycle and an interrogation and resonant frequency detection are performed only at the instant in time when the BSCC heart valve is changed from an open state to a fully closed state.

14. The method in accordance with claim 12 further comprising the BSCC heart valve opens and closes during a cardiac cycle and an interrogation and resonant frequency detection are performed during the cardiac cycle after the heart valve is closed and before the heart valve reopens.

* * * * *